United States Patent
Chivers et al.

[11] Patent Number: 5,942,276
[45] Date of Patent: Aug. 24, 1999

[54] METHOD OF MANUFACTURING X-RAY VISIBLE SOLUBLE COVERING

[75] Inventors: Bruce E. Chivers, Minneapolis; Mary M. Morris, Mounds View; Richard D. Sandstrom, Scandia, all of Minn.

[73] Assignee: Medtronic, Inc., Minneapolis, Minn.

[21] Appl. No.: 09/008,236

[22] Filed: Jan. 16, 1998

[51] Int. Cl.$^6$ .................................................. B05D 3/00
[52] U.S. Cl. ..................... 427/2.12; 427/2.24; 427/2.3; 427/58; 427/256; 427/385.5
[58] Field of Search ............... 427/2.12, 2.24, 427/2.3, 385.5, 256, 58

[56] References Cited

U.S. PATENT DOCUMENTS

| | | | |
|---|---|---|---|
| 3,819,480 | 6/1974 | Hochschild | 195/1.8 |
| 3,844,292 | 10/1974 | Bolduc . | |
| 4,289,144 | 9/1981 | Gilman . | |
| 4,475,560 | 10/1984 | Tarjan et al. . | |
| 4,506,680 | 3/1985 | Stokes . | |
| 4,827,940 | 5/1989 | Mayer et al. . | |
| 4,876,109 | 10/1989 | Mayer et al. . | |
| 4,972,848 | 11/1990 | DiDomenico et al. . | |
| 4,998,975 | 3/1991 | Cohen et al. . | |
| 5,092,332 | 3/1992 | Lee et al. . | |
| 5,282,844 | 2/1994 | Stokes et al. . | |
| 5,282,845 | 2/1994 | Bush et al. . | |
| 5,324,327 | 6/1994 | Cohen . | |
| 5,443,492 | 8/1995 | Stokes et al. . | |
| 5,531,783 | 7/1996 | Giele et al. . | |
| 5,683,447 | 11/1997 | Bush et al. . | |

*Primary Examiner*—Bernard Pianalto
*Attorney, Agent, or Firm*—Reed A. Duthler; Harold R. Patton

[57] ABSTRACT

A method of fabricating a radiopaque dissolvable covering for a member on an implantable lead, including the steps of mixing a radiopaque material with a solvent to form a paste, applying the paste to the member and allowing the paste to harden. The lead preferably is provided with a drug incorporated therein which is subject to degradation at high temperature, located adjacent to the member, and the applying step preferably takes place at about room temperature. The member to which the paste is applied may be an active fixation device such as a barb or a helix or may be a deployable member such as a tine or an electrode bearing member.

16 Claims, 1 Drawing Sheet

METHOD OF MANUFACTURING X-RAY VISIBLE SOLUBLE COVERING

BACKGROUND OF THE INVENTION

This invention relates to body implantable leads and, in particular, pacing leads having a distal fixation element for attachment to the inner wall of a patient's heart.

The efficacy of cardiac pacing has been widely accepted for some time now. As is well known, a pacing system comprises the basic combination of a generator, or pacemaker, and a lead. The pacemaker performs the basic function of generating pacing pulses, and also receives sensed heartbeat signals and other sensor signals for determining when pacing pulses are to be delivered and at what rate. The pacemaker is operatively connected to the heart tissue by the lead, which carries the generated pacing pulses to the heart and carries sensed heart signals from the heart back to the pacemaker. The pacing lead is fixed to the pacemaker at the proximal end by known techniques, and the distal end must be positioned at a desired location adjacent to heart wall in order to secure optimized chronic performance. In order to secure the distal end of the lead to the heart wall, many leads employ an anchoring element such as a helical coil, barbs or the like. A great many different anchoring elements are known in the art and are disclosed in the patent literature. For the purposes of this invention, the helix, or screw-in element, will be used as illustrative, it being understood that the invention is not limited and is applicable to other types of anchoring elements.

In practice, the physician must introduce the lead intravenously into the heart, position the distal tip adjacent the heart wall so that an optimum threshold is obtained and then, in the case of a lead with an active anchor element, secure the element into the heart wall. The intravenous introduction of the lead requires that the lead be flexible and small in diameter, and devoid of any protruding element or part which would hinder passage through the vein. Thus, the presence of a distal anchor element can carry the substantial disadvantage of making the intravenous insertion much more difficult. In order to overcome the disadvantage posed by the anchor element to the insertion process, a number of lead designs have been proposed and implemented, with varying degrees of success. Recently, there has been disclosed a cardiac pacing electrode having a soluble covering which surrounds the fixation helix which is mounted at the distal tip end. Such a covering has size, shape and solubility characteristics such that it maintains its smooth outer form during the transvenous insertion process, but thereafter dissolves so as to expose the anchor helix or other like anchor element. Reference is made to U.S. Pat. Nos. 4,827,940 and 4,876,109, which disclose such a soluble covering for a cardiac pacing electrode. The problem that remains with the covering as described in the aforementioned two patents, is that the implantation procedure is necessarily interrupted while the physician waits a sufficient time to permit full dissolution of the soluble coveting. In practice, the physician, or physician's assistant, has to either wait a specified time or make measurements such as impedance drop, before screwing the lead into the heart tissue. For an experienced and adept implanter, this introduces an annoying delay, since invariably it is necessary to overwait in order to ensure that the soluble covering has indeed dissolved. What is thus desired in the art is a lead with means for providing an instant indication as to when the covering has dissolved, so that the fixation element can be fixed to the heart wall without delay.

One approach to providing an indication as to when the covering has dissolved is disclosed in U.S. Pat. No. 5,531,783 issued to Giele et al., in which a mannitol covering is improved by having a contrast medium or like radiopaque material within at least a portion thereof to render it x-ray visible until it dissolves, whereby the lead tip can be monitored to determine first when the fixation element is proximate to the heart tissue, and particularly when the covering has dissolved. The process employed to fabricate the covering unfortunately requires a high temperature melting step and exposure of the lead to the mannitol covering while melted in order to apply the covering to the fixation element. Such high temperatures are particularly undesirable in leads which include a steroid drug for elution adjacent the fixation element in order to reduce pacing thresholds. Sodium dexamethasone phosphate, for example, is damaged by temperatures in excess of 140 degrees Fahrenheit. High temperatures may also cause decomposition of contrast media.

SUMMARY OF THE INVENTION

It is an object of this invention to provide an implantable lead, and in particular an implantable pacing lead which carries an active fixation element at its distal end, the lead having a covering or covering over the fixation element, the covering having characteristics to provide that it dissolves within a reasonable time upon insertion into the patient's heart. The lead further has means for providing a real time indication to the attending physician of when the covering has dissolved, so that the physician can proceed directly to fix the distal fixation element to the patient's heart wall, as soon as possible and with minimum delay. It is an additional object of the invention to provide an acceptable dissolvable covering without exposing the lead to elevated temperatures during the manufacturing process.

In accordance with the above objects, there is provided an implantable lead having distal and proximal ends and a flexible length between such ends, the lead having a fixation element at its distal end for effecting fixation of the lead to the inside of the heart wall, the lead having a covering over at least a portion of the fixation element to provide a smooth outer surface so as to facilitate insertion of the lead transvenously into the heart. The covering is soluble in body fluids and has dissolving or dissolution characteristics selected so that it dissolves only after being in the body fluids for at least a predetermined time. The covering has a radiopaque contrast medium or like material within at least a portion thereof to render it x-ray visible until it dissolves, whereby the lead tip can be monitored to determine first when the fixation element is proximate to the heart tissue, and particularly when the covering has dissolved.

The covering is improved in that it is manufactured using a process which can be carried out without exposing the lead to elevated temperatures, which in turn simplifies manufacture of the lead. Steroids or other temperature sensitive drugs may be incorporated into the lead either adjacent to the fixation element prior to application of the covering to the fixation element without fear of damage due to high temperatures, and the risk of decomposition of the contrast medium is avoided. In a preferred embodiment, the lead includes a monolithic controlled release device for delivering sodium dexamethasone phosphate and the covering is manufactured at room temperature or slightly above.

In the practice of this invention, using a pacing lead, the physician inserts the lead transvenously to the point where the distal tip is in the patient's heart. The physician monitors the radiopaque material, and upon seeing that the material has dissolved, proceeds directly to attach the distal tip to the heart wall.

DESCRIPTION OF THE PREFERRED EMBODIMENTS

Figures 1A, 1B, 1C:
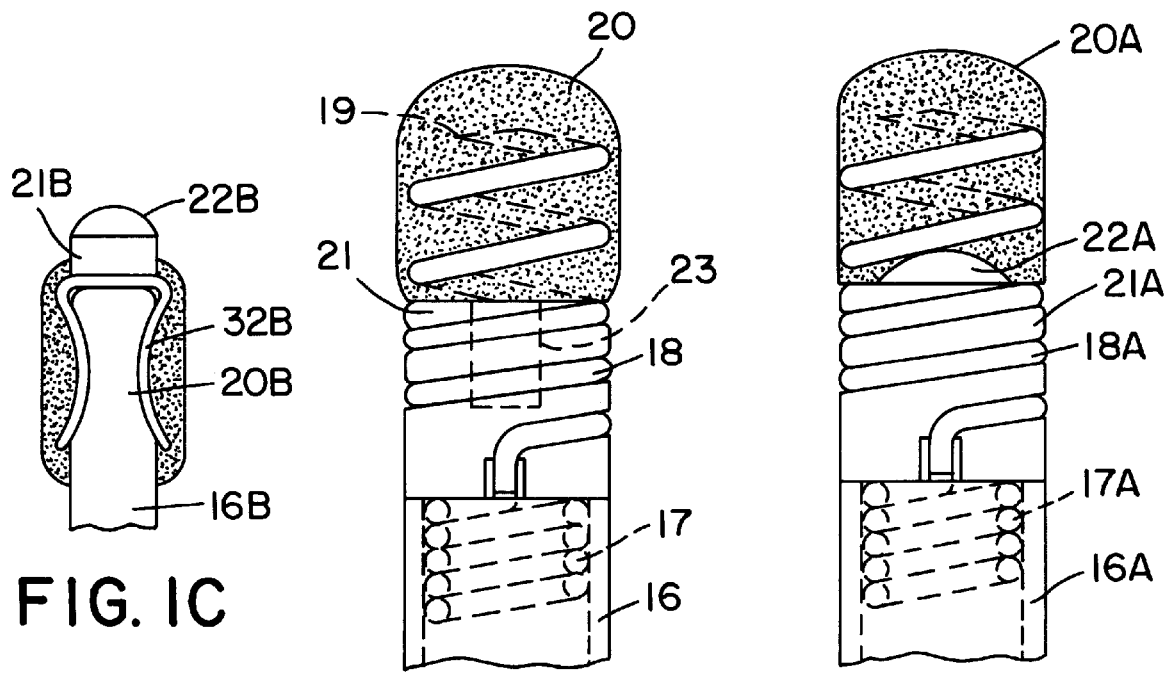
FIG. 1A is a diagrammatic representation of the distal tip end of a lead in accordance with this invention.
FIG. 1B is a diagrammatic representation of the distal tip end of an alternate embodiment, of the invention.
FIG. 1C is a representation of a lead where the covering covers tines in a folded position until it dissolves.

Referring now to FIG. 1A, there is shown a representation of the distal end portion of a lead in accordance with this invention. The lead has a lead body 16, running substantially the length of the lead from the proximal to the distal end, and a coiled conductor 17 which provides transmission of electrical signals from the proximal to distal end, and vice versa. Coil 17 is connected mechanically and electrically at the distal tip end to a helical fixation element 18, as illustrated. Helix 18 may be, as illustrated here, a distal electrode as well as a fixation element. The distal end portion 21 of lead body 16 may have incorporated therein a glucocorticosteriod drug such as sodium dexamethasone phosphate, either incorporated into the lead body itself as in U.S. Pat. No. 5,092,332, issued to Lee et al, incorporated herein by reference in its entirety, or incorporated into a monolithic controlled release device 23, shown in broken line outline, for example as disclosed in U.S. Pat. No. 4,972,848, issued to DiDomenico et al., also incorporated herein by reference in its entirety.

As illustrated in FIG. 1A, the helix 18 has a terminating end 19 which has an appropriately sharp tip so as to aid screwing of the helix into the heart wall. The portion of helix 18 which is to be free for screwing into the heart wall is embedded in and covered by a covering 20, as illustrated, which is shaped so as to provide smooth passage of the distal end of the lead through the patient's veins. The process for producing the covering is described in more detail below. These covering dissolves when placed in body fluids, i.e. blood, within a predetermined time, e.g., about 3–4 minutes and is non-toxic and biocompatible in all respects. Further in accordance with this invention, the covering includes a radiopaque material, which is x-ray visible until the covering is dissolved. By constantly monitoring the distal tip as it is positioned within the heart, the physician doing the procedure can know instantly when the helix is free for insertion into the heart wall, and proceed directly to take the step of screwing it into the heart wall.

Referring to FIG. 1B, there is shown an alternate embodiment wherein a pacing electrode 22A separate from the helix 18A is provided. Electrode 22A is coupled to coil 17A and extends out the distal portion 21A of lead body 16A. Electrode 22A, for example, may be a steroid eluting electrode as disclosed in U.S. Pat. No. 5,282,844, issued to Stokes et al or U.S. Pat. No. 4,506,680, issued to Stokes, both incorporated herein by reference in their entireties. Covering 20A corresponds to covering 20 (FIG. 1A).

While the embodiments of FIGS. 1A and 1B employ metal helices as fixation members, other active fixation members such as barbs, hooks or the like may be substituted and provided with the improved covering of the present invention. For example, active fixation devises as disclosed in U.S. Pat. No. 5,683,447, issued to Bush et al., U.S. Pat. No. 5,443,492, issued to Stokes et al., U.S. Pat. No. 3,844, 292, issued to Bolduc or U.S. Pat. No. 4,475,560, issued to Tarjan et al., all incorporated herein by reference in their entireties might be employed.

In another embodiment as shown in FIG. 1C, the fixation element may be resilient plastic tines as are conventionally used in pacing leads, and the covering 20B covers the tines 32B so as to hold them folded against the lead body 16B until the covering dissolves. Tines 32B are located slightly proximal of electrode 22b, which may be a steroid eluting electrode corresponding to electrode 22A (FIG. 1B). Covering corresponds to covering 20 (FIG. 1A). After the covering dissolves, the tines resiliently expand outward away from the lead body. The covering of the present invention may also be employed to retain other deployable or expandable members folded against the lead body or against each other, including members carrying electrodes, as in U.S. Pat. No. 5,282,845, issued to Bush et al., U.S. Pat. No. 5,324,327, issued to Cohen, U.S. Pat. No. 4,998,975, issued to Cohen or U.S. Pat. No. 4,289,144, issued to Gilman, all incorporated herein by reference in their entireties. In such embodiments the covering may be applied to completely surround the expandable members or may be employed to adhere the expandable members to the lead body and/or to each other.

The following is an illustrative example of a method of preparing the distal tip end of a lead so as to provide a suitable covering which protects and shields the anchor element, wherein the covering is suitably soluble and provides the desired angiographic contrast and wherein the manufacturing process does not involve exposure of the distal end of the lead body to high temperatures.

The covering according to the present invention is preferably made by mixing a powdered form of the active ingredient in an angioplasty contrast media, such as ioversol, sold as "Optiray" by Mallincrodt, Inc. mixed with a solvent, such as water to produce a paste. The paste in this form consists of a saturated solution of ioversol in water with additional ioversol powder. The paste may be extruded into a small mold, for example made from silicone rubber, and defining the desired shape the covering is to assume while on the lead body or may otherwise be formed into a body having the desired configuration. If the covering is to cover a fixation helix, the paste is preferably allowed to dry for some time to begin hardening, after which the fixation helix may be screwed into the paste while still semi-solid. If the covering is to be applied to a deployable mechanism such as tines, the paste may first be inserted in the mold and the distal end of the lead body is inserted thereafter, displacing excess paste. After drying at room temperature or slightly above room temperature, the silicone mold is flexed, allowing removal of the distal end of the lead with the hardened covering.

The covering manufactured in this fashion has the advantage that applying the covering to the distal end of the lead does not require high temperature melting steps, so that damage to the lead body and/or to any temperature sensitive drugs incorporated therein is avoided. Damage to the radiopaque material is also avoided, as the covering is fabricated at temperatures well below those which might damage commercially available contrast media.

The covering may also be fabricated by simply mixing deionized water and ioversol in proportions sufficient to produce a formable paste, rolling the formed paste into a ball and screwing the ball onto the fixation helix at the end of a pacing lead, and allowing the covering to dry. An alternative mechanism for fabricating the covering is to mix ioversol and deionized water to produce a saturated solution of ioversol, allowing the saturated solution to dry for approximately two hours and thereafter injecting it into a mold. The fixation helix at the end of a cardiac pacing lead may then be screwed into the paste in the mold and allowed to dry overnight. The mold may then be removed from the fixation helix. An additional alternative is to mix, for example, one gram of ioversol powder to each 0.2 cc. of deionized water to form a paste, thereafter rolling the paste to form a ball and rolling the ball in ioversol powder to cover the entire outer surface and reduce the tackiness of the paste. The paste may then be applied to the fixation helix, tines or other expandable members to cover them and allowed to dry at room temperature or slightly above.

Coverings fabricated according to the above procedures and applied to fixation helixes of the types typically employed in cardiac pacing leads displayed times to dissolution in saline at 100° F. of approximately three to seven minutes, depending upon the mass of the covering applied.

The radiopaque material employed in the context of the present invention is preferably a water soluble, iodine based contrast medium such as ioversal, discussed above. Other such contrast media include Iohexol, manufactured by Nycomed and Iotrolan, manufactured by Scherling. The radiopaque material may be mixed with water as discussed above or with other solvents such as alcohols, provided the material is soluble therein.

Figure 2:
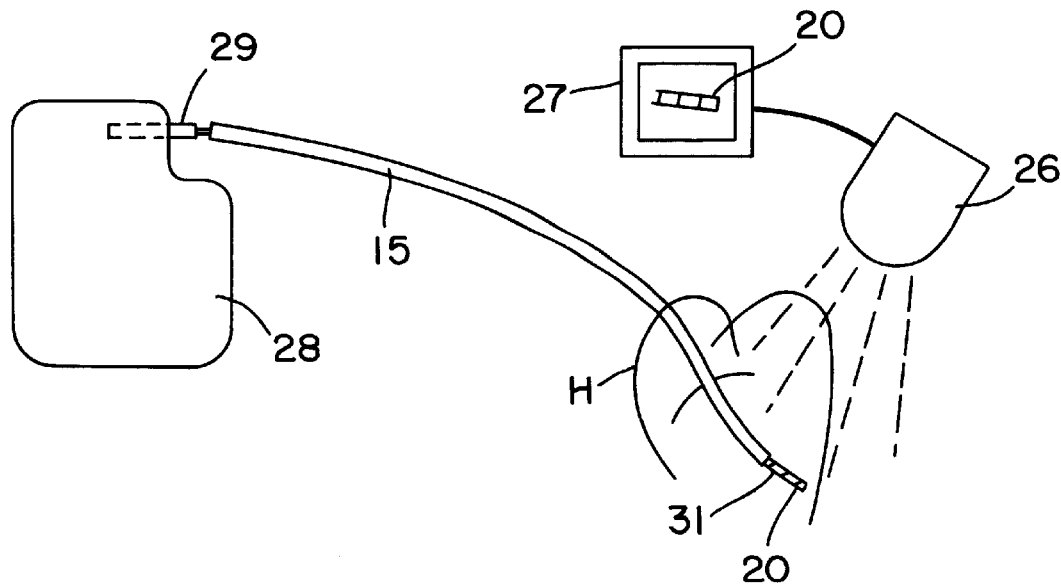
FIG. 2 is a system block diagram illustrating the lead of this invention in combination with a pacemaker and x-ray equipment.

Referring now to FIG. 2, there is shown a schematic representation of a pacing and monitoring system in accordance with this invention. The lead 15 is illustrated having a proximal end pin 29 which is inserted into and mechanically and electrically connected to pacemaker 28. Coil conductor 17 is electrically connected to pin 29, so as to provide electrical connection between the pacemaker and the distal end of the lead. The lead 15 is inserted, as discussed above, into the heart H, so that the covering 20 is positioned at a desirable location adjacent to heart wall. There is illustrated an electrode 31 which, as discussed above, may be the helical element or may be a separate element mounted at the distal tip. Also shown is X-ray monitoring device 26, interconnected with a monitor 27. By watching the image on monitor 27, the physician can determine when the covering 20 has dissolved, such that fixation can be accomplished. It is to be noted that the procedure has the further advantage of permitting the physician to monitor the path of the distal tip as it is inserted into the heart, thereby aiding the positioning of the distal tip at a desired location adjacent the heart wall.

In conjunction with the above disclosure, we claim:

1. A method of fabricating a radiopaque dissolvable covering for a member on an implantable lead, comprising:
   mixing a radiopaque material with a solvent to form a paste;
   applying said paste to said member; and
   allowing said paste to harden; and
   wherein said applying step comprises applying said paste to a deployable member mounted to said lead.

2. A method according to claim 1 wherein said step of applying said paste and allowing said paste to harden are carried out at about room temperature.

3. A method according to claim or claim 1 wherein said step of applying said paste comprises applying said paste to a member of a lead having a drug incorporated therein which is subject to degradation at greater than a first temperature, located adjacent said member, and wherein said applying step takes place at less than said first temperature.

4. A method according to claim 1 wherein said mixing step comprises mixing a contrast medium and said step of applying said paste to said member of a lead takes place at a temperature less than said that which might damage the contrast medium.

5. A method according to claim 1 wherein said applying step comprises applying said paste to a deployable barb mounted to said lead.

6. A method according to claim 5 or claim 1 wherein said applying step comprises applying said paste to a member mounted to a lead having sodium dexamethasone phosphate incorporated therein adjacent said member and wherein said applying step takes place at less than 140 degrees Fahrenheit.

7. A method of fabricating a radiopaque dissolvable covering for an member on an implantable lead, comprising:
   mixing a radiopaque material with a solvent to form a paste;
   applying said paste to said member; and
   allowing said paste to harden; and
   wherein said applying step comprises applying said paste to an active fixation device, mounted to said lead.

8. A method according to claim 7 wherein said applying step comprises applying said paste to a fixation helix, mounted to said lead.

9. A method of fabricating a radiopaque dissolvable covering for an active fixation device on a lead for implant in a patient's heart, comprising:
   mixing a powdered contrast medium with a solvent to form a paste;
   applying said paste to said active fixation device; and
   allowing said paste to harden.

10. A method according to claim 9 wherein said mixing step comprises mixing a powdered contrast medium with a solvent to form a paste consisting essentially of said contrast medium and said solvent.

11. A method according to claim 9 or claim 10 wherein said step of applying said paste comprises applying said paste to an active fixation device of a lead having a drug incorporated therein which is subject to degradation at greater than a first temperature, located adjacent said member, and wherein said applying step takes place at less than said first temperature.

12. A method according to claim 9 or claim 10 wherein said step of applying said paste and allowing said paste to harden are carried out at about room temperature.

13. A method of using a lead having an active fixation device, comprising:
   mixing a powdered contrast medium with a solvent to form a paste;
   applying said paste to said active fixation device;
   allowing said paste to harden;
   advancing said lead into a patient's heart;
   allowing said paste to dissolve; and
   engaging said patient's heart with said active fixation device.

14. A method according to claim 13 wherein said mixing step comprises mixing a powdered contrast medium with a solvent to form a paste consisting essentially of said contrast medium and said solvent.

15. A method according to claim 13 or claim 14 wherein said step of applying said paste comprises applying said paste to an active fixation device of a lead having a drug incorporated therein which is subject to degradation at greater than a first temperature, located adjacent said member, and wherein said applying step takes place at less than said first temperature.

16. A method according to claim 13 or claim 14 wherein said step of applying said paste and allowing said paste to harden are carried out at about room temperature.

* * * * *